United States Patent [19]

Rossoff

[11] Patent Number: 5,183,031
[45] Date of Patent: Feb. 2, 1993

[54] FIBEROPTIC INTUBATING LARYNGOSCOPE

[76] Inventor: Leonard J. Rossoff, 270-05 76th Ave.; Suite C-20, New Hyde Park, N.Y. 11042

[21] Appl. No.: 699,488
[22] Filed: May 13, 1991
[51] Int. Cl.$^5$ ............................................... A61B 1/06
[52] U.S. Cl. ................................................ 128/6; 128/11
[58] Field of Search ........................ 128/4, 5, 6, 10, 11

[56] References Cited

U.S. PATENT DOCUMENTS 3,913,568  10/1975  Carpenter ................................ 128/11
4,598,698   7/1986  Siegmund ................................. 128/4
4,617,915  10/1986  Arakawa .................................. 128/4

Primary Examiner—J. Wilson
Assistant Examiner—Jeffrey A. Smith
Attorney, Agent, or Firm—Michael I. Kroll

[57] ABSTRACT

The present invention relates to a fiberoptic intubating laryngoscope attachable to a stylet. The fiberoptic intubating laryngoscope includes a pistol grip, a universal adaptor and a beveled junction and attaching the stylet to the pistol grip, the universal adaptor having vents, an oxygen port disposed on the pistol grip to allow for continuous flushing of oxygen through an endotracheal tube via the vents in the universal adaptor, a fiberoptic bundle passing through the stylet, a suction channel passing through the stylet, a light source disposed within the pistol grip, an optical head connected to the pistol group for direct visualization by the user, and a syringe port disposed on a suction inlet on the pistol grip and allowing a syringe to inject a topical anesthetic via the suction channel.

8 Claims, 1 Drawing Sheet

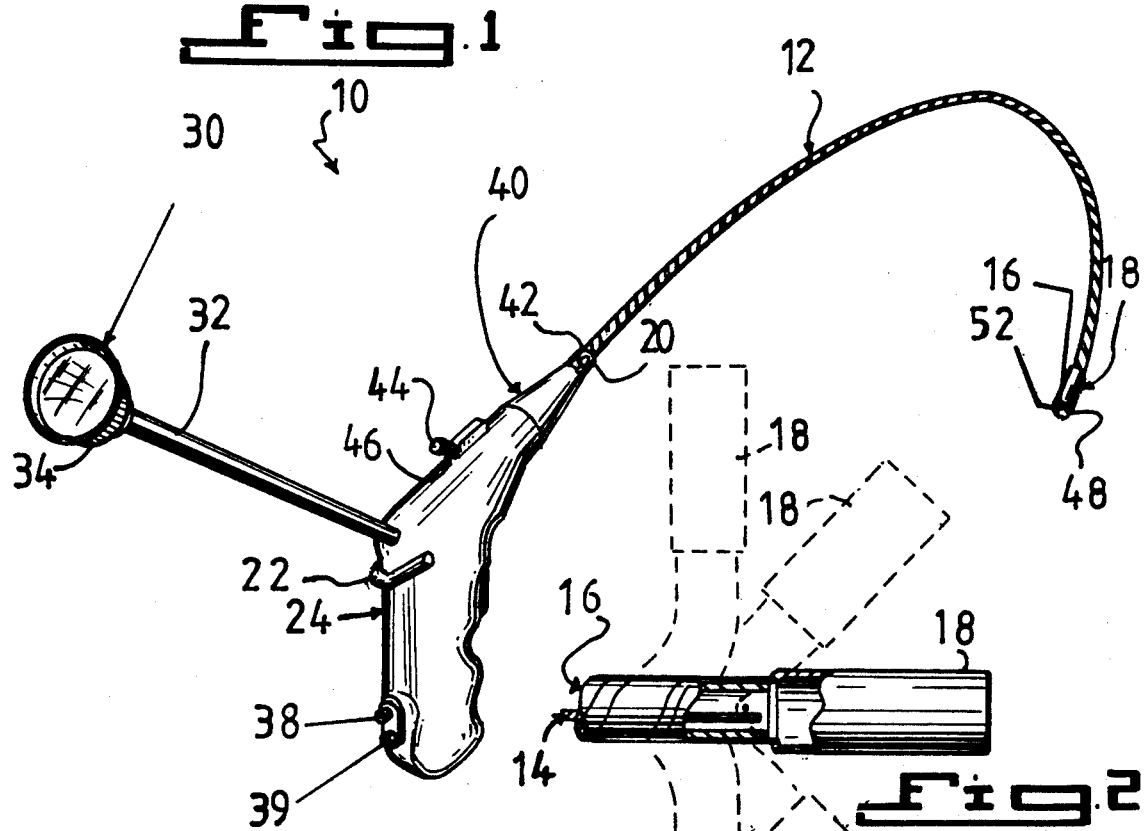
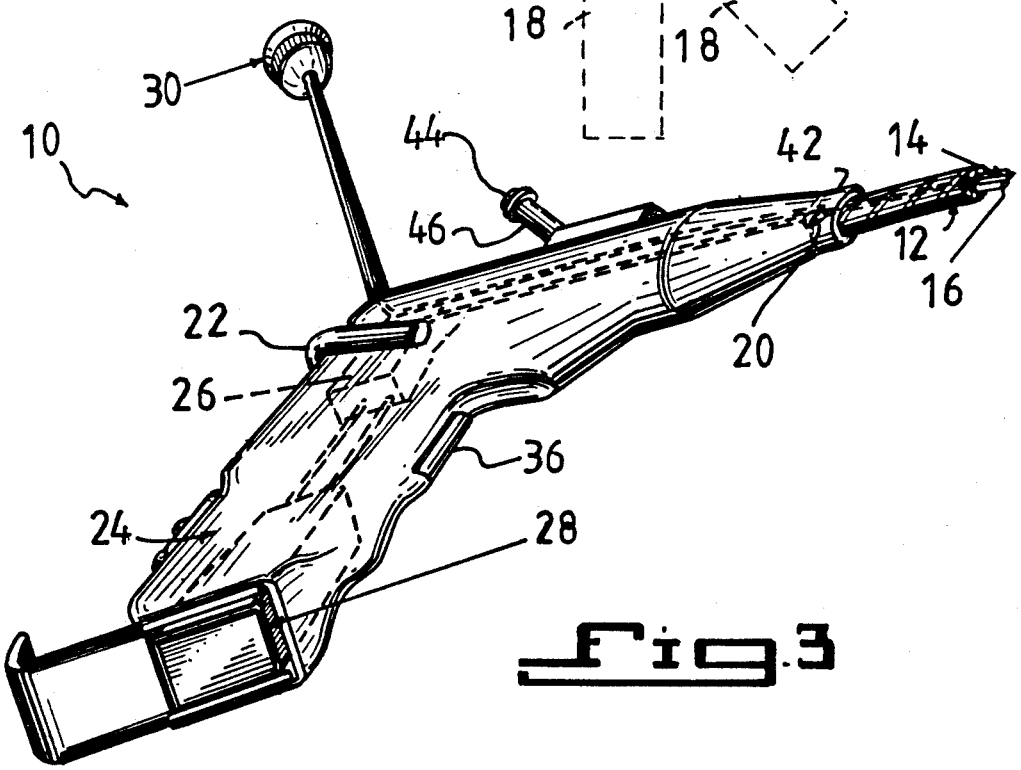

FIBEROPTIC INTUBATING LARYNGOSCOPE

BACKGROUND OF THE INVENTION

1. Field of the Invention

The present invention relates to an intubating laryngoscope.

More particularly, the present invention relates to a fiberoptic intubating laryngoscope that allows for orotracheal or nasotracheal intubation of patients using a wide variety of standard endotracheal tubes under direct vision.

2. Description of the Prior Art

Current endotracheal intubation is effected in the vast majority of cases by use of a laryngoscope with a straight or curved metal blade. The curved blade is inserted between the epiglottis and the base of the tongue and the straight blade under the epiglottis, with a forward and upward motion required. Landmarks for insertion of the tube are the epiglottis, arytenoid cartilages and the vocal cords which may be only partially or not at all visualized. In the absence of direct visualization of the cords, difficulties in intubation may occur in the following and other circumstances: short muscular neck with full set of teeth; receding lower jaw; tempero-mandibular disease; long high-curved palate; difficulty in posturing of head and neck and opening of jaw (e.g. rheumatoid and asteoarthritis, suspected cervical spine injuries, and trismus); and masses or foreign bodies in the pharynx or larynx.

If a difficult intubation is anticipated, usually in elective and non-emergent situations only, intubation can be effected over a conventional fiberoptic bronchoscope or laryngoscope. These, however, are not widely available and very delicate instruments requiring significant expertise in their use. Their construction makes the intubation extremely awkward particularly when an orotracheal intubation is contemplated.

Numerous innovations for fiberoptic intubating laryngoscope have been provided in the prior art that are adapted to be used. Even though these innovations may be suitable for the specific individual purposes to which they address, they would not be suitable for the purposes of the present invention as heretofore described.

SUMMARY OF THE INVENTION

Accordingly, it is an object of the present invention to provide fiberoptic intubating laryngoscope that avoids the disadvantages of the prior art.

More particularly, it is an object of the present invention to provide a fiberoptic intubating laryngoscope that allows for direct visualization of the cords via a fiberoptic system.

The fiberoptic intubating laryngoscope of the present invention is inserted into a standard endotracheal tube allowing for an initial stable "stylet" like shaping of the tube as well as flexion and extension of the tip of the tube in one plane by a hardy cable system. The endotracheal tube can be fully lubricated without loss of control.

Additionally, oxygen can be flushed through the present invention during the actual intubation. This feature is not found on conventional bronchoscopes or laryngoscopes because of their multipurpose design. The spraying of local anesthetic is also possible through the common suction channel. Additionally, a standard endotracheal tube with or without its universal adapter may be secured to a beveled junction or male universal adapter. This feature is not found on conventional bronchoscopes because of their multipurpose design. Correct positioning of the tube can be confirmed by direct visualization of the carina, thereby precluding the need of an immediate postintubation radiograph.

The advantages of the present invention over the conventional available laryngoscopes, fiberoptic endoscopes and previous devices include: rapid intubation under direct vision; application of suction simultaneous to insertion of endotracheal tube; complete visualization and, therefore, minimization of damage to the glottis and vocal cords; institution of liquid local anesthetics in advance and during insertion of the endotracheal tube; assurance of proper positioning of endotracheal tube relative to carina precluding need of an immediate post-intubation radiograph; avoidance of right mainstem intubation; selective intubation of right or left mainstem bronchus if medically indicated; allowance for difficult intubation without need of repositioning of neck; obedient steel stylet allows reshaping and support of endotracheal tube unlike conventional and modified fiberoptic scopes facilitating its guidance especially by less experienced operator, while allowing for lubrication of exterior of endotracheal tube along its entire length without loss of control, retaining sufficient flexibility to negotiate bends in the oro and nasopharynx; stylet's position within the soft endotracheal tube minimizes potential for dental and oropharyngeal damage; rugged construction allows for easy cold sterilization as well as gas sterilization; rugged construction as well as stability allows for use by less experienced operators; rugged construction allows the instrument to be utilized in all the same settings of the steel bladed laryngoscope (e.g. crash carts, ER, ICU, etc.).

In keeping with these objects, and with others which will become apparent hereinafter, one feature of the present invention resides, briefly stated, in a fiberoptic intubating laryngoscope comprising a pistol grip, a beveled junction leading to a universal adaptor with vents attachable to a stylet, an oxygen port disposed on the pistol grip to allow for continuous flushing of oxygen via these vents in the universal adaptor, a fiberoptic bundle passing through the stylet, a suction channel passing through the stylet, a suction port disposed on the pistol grip to allow for suction through the suction channel controlled by a trigger disposed on the pistol grip, and a syringe port disposed on top of the pistol grip allowing a syringe to inject a topical anesthetic via the suction channel, a light source disposed within the pistol grip, an optical head connected to the pistol grip for direct visualization by the user.

In accordance with another feature of the present invention, the pistol grip is approximately 6 inches long.

Another feature of the present invention is that it further comprises a lever pivotally attached to the pistol grip for controlling the distal end of the stylet.

Yet another feature of the present invention is that it further comprises batteries for the power source and being disposed in the pistol grip.

Still another feature of the present invention is that it further comprises a stem which is approximately 5 inches long and connects the optical head to the pistol grip.

Yet still another feature of the present invention is that the optical head is equipped with a focus ring.

Still yet another feature of the present invention is that it further comprises a suction trigger, a suction port, and a suction inlet with syringe port, the suction trigger, the suction port, and the suction inlet with port being disposed on the pistol grip so a to provide for continuous or intermittent suction through the suction channel and irrigation of fluids through the same channel.

Another feature of the present invention is that the pistol grip is designed to allow for both right and left handed operation.

The novel features which are considered characteristic for the invention are set forth in particular in the appended claims. The invention itself, however, both as to its construction and its method of operation, together with additional objects and advantages thereof, will be best understood from the following description of the specific embodiments when read in connection with the accompanying drawing.

BRIEF DESCRIPTION OF THE DRAWING

FIG. 1 is a top perspective view of the fiberoptic intubating laryngoscope of the present invention;

FIG. 2 is a side view showing the range of motion of the last ⅓ of the flexible tube of FIG. 1; and FIG. 3 is a bottom perspective view of the fiberoptic intubating laryngoscope of the present invention shown in FIG. 1.

LIST OF REFERENCE NUMERALS UTILIZED IN THE DRAWING

10—fiberoptic intubating laryngoscope
12—"goose neck" stylet
14—fiberoptic bundle
16—suction channel
18—distal tip
20—vents
22—lever
24—pistol grip
26—light source
28—rechargeable or disposable batteries
30—optical head
32—stem
34—focus ring
36—suction valve or trigger
38—suction port
39—oxygen port
40—beveled junction
42—universal adaptor
44—syringe port
46—suction inlet
48—distal tip
52—fiberoptic lens

DETAILED DESCRIPTION OF THE PREFERRED EMBODIMENT

The fiberoptic intubating laryngoscope of the present invention 10 is approximately 13 inches long with a 0.2 inch diameter vinyl clad flexible and obedient steel tube "goose neck" stylet 12 enclosing a fiberoptic bundle 14 and a suction channel 16. The distal tip 18 is approximately 1 inch, is flexible up and down in one plane in a narrow range of motion and manipulated by a cable (not shown) operated by a lever 22 on a pistol grip 24.

The pistol grip houses a light source 26 and rechargeable or disposable batteries 28. An optical head 30 mounted on a stem 32 approximately 5 inches from the grip 24 is equipped with a focus ring 34.

A valve or trigger 36, port 38, and inlet 46 with syringe port 44 are also provided to allow for continuous or intermittent suction and/or the instillation of fluids (e.g. topical anesthetic) through the common channel 16. An oxygen port 39 is also provided in the grip 24 to allow for continuous flushing of oxygen through the endotracheal tube via vents 20 on the male universal adaptor 42 of the "gooseneck" tube 12 through the beveled junction 40 to the pistol grip 24. The beveled junction 40 allows for secure attachment of the proximal end of a standard endotracheal tube without its female universal adaptor of a standard endotracheal tube. Oxygen delivery and suction, if required, can be provided by standard commercial devices and tubing.

The distal tip 18 of the "goose neck" tubing 12 and can be forcefully flexed and extended through a narrow range by the lever 22 with a hearty cable system (not shown) similar to that in a standard fiberoptic endoscope. A standard topical anesthetic syringe (not shown) can be injected through the suction channel 16 via a syringe port 44 on the suction inlet 46 on top of the pistol grip 24 similar to that in a standard fiberoptic endoscope.

In operation, the standard endotracheal tube of most sizes is inserted over the "goose neck" stylet 12 and its proximal end secured to the beveled junction 40 or its female universal adaptor to the male universal adaptor 42. Endotracheal tube may then be lubricated along its entire length by a standard lubricant or anesthetic jelly. The "goose neck" stylet 12 and endotracheal tube are then bent to the desired shape. The endotracheal tube is then inserted nasotracheally or orotracheally under direct vision to the larynx. Movement is effected by simple rotation of the handle 24 and flexion of the tip 18. When the larynx is approached, the endotracheal tube tip is positioned by the flexible tip 18 via the fiberoptic lens 52 to fully visualize the cords. When the cords are fully visualized, the stylet 12 and endotracheal tubes may be advanced into the trachea. The endotracheal tube is properly positioned under direct vision at the proper distance from the carina. The endotracheal tube is then firmly gripped and secured and the "goose neck" stylet 12 withdrawn. The endotracheal tube then may be shortened, taped or secured in the conventional manner.

The patient can be continuously provided with oxygen during intubation as well as suctioned with direct vision of the user. The syringe port 44 on the suction inlet 46 allows for adequate topical anesthesia particularly in the non-emergent conditions. The present invention 10 is designed to allow for both right and left handed operation. Unlike conventional laryngoscopes and most fiberoptic scopes, the patients are treated from the side and not from behind. Therefore, the headboard, if present, need not be removed.

It will be understood that each of the elements described above, or two or more together, may also find a useful application in other types of constructions differing from the type described above.

While the invention has been illustrated and described as embodied in a fiberoptic intubating laryngoscope, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A fiberoptic intubating laryngoscope comprising:
   a) a pistol grip having a stylet attached there to;
   b) a suction channel passing through said stylet;
   c) an optical head with a lens and being connected to said pistol grip for direct visualization by the user;
   d) a universal adaptor having a beveled junction said universal adaptor having vents, the location of said vents being more proximally on said universal adaptor providing for less resistance and therefore greater flow of oxygen without comprising the size of said suction channel;
   e) an oxygen port disposed on said pistol grip to allow for continuous flushing of oxygen via said vents in said universal adaptor, said oxygen is flushed continuously through said vents at a distal tip of said bevelled universal adaptor, said continuous flushing of oxygen keeps said lens clear of secretions encountered in endoscopy and intubation;
   f) a fiberoptic bundle passing through the stylet;
   g) a light source disposed within said pistol grip; and
   h) a syringe port disposed on a suction inlet disposed on said pistol grip and allowing a syringe to inject a topical anesthetic via said suction channel.

2. A laryngoscope as defined in claim 1 wherein said pistol grip is approximately 6 inches long.

3. A laryngoscope as defined in claim 2; further comprising a lever pivotally attached to said pistol grip for controlling the stylet.

4. A laryngoscope as defined in claim 3; further comprising batteries for said power source and being disposed in said pistol grip.

5. A laryngoscope as defined in claim 4; further comprising a stem which is approximately 5 inches long and connects said optical head to said pistol grip.

6. A laryngoscope as defined in claim 5, wherein said optical head is equipped with a focus ring.

7. A laryngoscope as defined in claim 6; further comprising a suction trigger, a suction port, said suction trigger, and said suction port, being disposed on said pistol grip so as to provide for continuous or intermittent suction through said suction channel.

8. A laryngoscope as defined in claim 7, wherein said pistol grip is designed to allow for both right and left handed operation.

* * * * *